United States Patent
Kido et al.

(10) Patent No.: US 9,540,420 B2
(45) Date of Patent: Jan. 10, 2017

(54) MUCOSAL VACCINES

(75) Inventors: Hiroshi Kido, Tokushima (JP); Dai Mizuno, Tokushima (JP)

(73) Assignee: TOKUSHIMA UNIVERSITY, Tokushima-shi, Tokushima (JP)

( * ) Notice: Subject to any disclaimer, the term of this patent is extended or adjusted under 35 U.S.C. 154(b) by 751 days.

(21) Appl. No.: 13/582,160

(22) PCT Filed: Mar. 1, 2011

(86) PCT No.: PCT/JP2011/054586
§ 371 (c)(1),
(2), (4) Date: Nov. 1, 2012

(87) PCT Pub. No.: WO2011/108521
PCT Pub. Date: Sep. 9, 2011

(65) Prior Publication Data
US 2013/0045232 A1     Feb. 21, 2013

(30) Foreign Application Priority Data
Mar. 2, 2010   (JP) ................. 2010-045205

(51) Int. Cl.
| | | |
|---|---|---|
| *A61K 39/395* | (2006.01) | |
| *C07K 14/005* | (2006.01) | |
| *A61K 9/00* | (2006.01) | |
| *A61K 39/145* | (2006.01) | |
| *A61K 39/12* | (2006.01) | |
| *A61K 39/00* | (2006.01) | |
| *A61K 47/32* | (2006.01) | |

(52) U.S. Cl.
CPC ........... *C07K 14/005* (2013.01); *A61K 9/0043* (2013.01); *A61K 39/12* (2013.01); *A61K 39/145* (2013.01); *A61K 39/00* (2013.01); *A61K 47/32* (2013.01); *A61K 2039/541* (2013.01); *A61K 2039/543* (2013.01); *A61K 2039/55516* (2013.01); *A61K 2039/55555* (2013.01); *A61K 2039/55561* (2013.01); *C12N 2760/16122* (2013.01); *C12N 2760/16134* (2013.01)

(58) Field of Classification Search
None
See application file for complete search history.

(56) References Cited

U.S. PATENT DOCUMENTS

| | | | |
|---|---|---|---|
| 6,635,246 B1 * | 10/2003 | Barrett et al. ............... | 424/93.6 |
| 8,287,887 B2 * | 10/2012 | Kido et al. ................. | 424/278.1 |
| 2004/0259201 A1 * | 12/2004 | Clark et al. ................. | 435/69.1 |

FOREIGN PATENT DOCUMENTS

EP          1930025     *  4/2006

* cited by examiner

*Primary Examiner* — Yunsoo Kim
(74) *Attorney, Agent, or Firm* — Wenderoth, Lind & Ponack, L.L.P.

(57) ABSTRACT

A mucosal vaccine producing an antigen-specific mucosal IgA and a blood IgG in the levels capable of exerting an effective immune induction and an infection-preventing effect, which comprises:
(a) an AD vehicle consisting of a synthetic peptide and a lipid(s), wherein the synthetic peptide consisting of the amino acid sequence KnLm (wherein n is 4 to 8 and m is 11 to 20);
(b) a carboxyvinyl polymer; and,
(c) an antigenic protein, in an amount incapable of producing a sufficient mucosal IgA and blood IgG for exerting an effective immune induction and an infection-preventing effect when used by itself.
The mucosal vaccine of the invention has an antibody producing ability which is more potent than those of mucosal vaccines of the prior art, and as a result it can exert an excellent effect even with an extremely small amount of an antigen.

7 Claims, 5 Drawing Sheets

MUCOSAL VACCINES

TECHNICAL FIELD

The present invention relates to a mucosal vaccine inducing a mucosal IgA and a blood IgG effectively.

BACKGROUND ART

Patent Documents 1 and 2 made detailed descriptions of the demerits in conventional inactivated vaccines or toxoids, as well as the current states with regard to the development of mucosal vaccines and immunoadjuvants.

As described in Patent Documents 1 and 2, the requirement of switching from a conventional vaccine of being inoculated subcutaneously or intramuscularly to a mucosal vaccine inducing the production of an IgA antibody on mucosa which is a natural viral infection route, is widely and profoundly recognized. Especially as a next generation vaccine in the 21st century, a mucosal vaccine inducing IgA antibody production, topical immunity or mucosal immunity is desired to be developed and brought into practical use all over the world, but it has not be achieved yet.

In response to these problems, the present inventors have invented an antigen-drug (AD) vehicle, which is a complex of a pulmonary surfactant protein B and/or a pulmonary surfactant protein C and a lipid(s), and a mucosal vaccine consisting of this AD vehicle and an antigen (Patent Document 1). The present inventors also found that by adjusting the weight ratio V/A of the AD vehicle amount (V) to the antigen amount (A), the selective production of an IgA antibody and the production of both IgA and IgG antibodies are convertible, and then developed a mucosal vaccine based on such action mechanism (Patent Document 2). Patent Documents 1 and 2 also disclose the effectiveness of fragments (peptides) of the pulmonary surfactant proteins B and C.

In addition, as a result of a study on various variants of pulmonary surfactant protein fragments for their antibody production enhancing effects, the present inventors have invented an AD vehicle comprising as a component a synthetic peptide KnLm (wherein n is 4 to 8 and m is 11 to 20) which, in spite that it is a smaller-sized peptide than the partial peptides disclosed in Patent Documents 1 and 2, has a potent antibody production-inducing or -enhancing effect, especially for an exclusive production of a secretory IgA antibody as well as an excellent and effective inductory effect on the production of both secretory IgA and blood IgG, and a mucosal vaccine consisting of this AD vehicle and an antigen (Patent Document 3).

In a nasal drop formulation whose administration route is identical to that for a mucosal vaccine, for the purpose of increasing the viscosity to sustain the efficacy against a pollinosis or an allergy, a carboxyvinyl polymer (CVP) or a hydroxypropyl cellulose (HPC) is employed widely and a thickening gelator such as sodium alginate is also employed. For example, an HPC-containing mucosal vaccine (Patent Document 4), a CVP-containing mucosal vaccine formulation (Patent Document 5) and an influenza vaccine for nasal spray (Patent Document 6) are also known. Patent Document 7 also discloses a mucosal vaccine consisting of an antigen, an adjuvant [especially Poly(I:C)] and a thickening agent (sodium alginate and the like).

Patent Document 1: WO 2005/097182
Patent Document 2: WO 2007/018152
Patent Document 3: WO 2009/123119
Patent Document: JP-A-2008-231343
Patent Document 5: WO 01/017556
Patent Document 6: JP-A-03-38529
Patent Document 7: JP-A-2009-209086

SUMMARY OF THE INVENTION

Problems to be Solved by the Invention

While the mucosal vaccine of Patent Document 3 has a potent antibody producing ability, it has a drawback, in common with other mucosal vaccines, that it requires an antigen in an amount larger than that in a percutaneously injectable vaccine.

For an effective vaccine treatment, a vaccine in an amount sufficient for the prevalence areas of its target infection should be required, but in view of the current antigen production scale it is difficult to produce an increased amount of the mucosal vaccine. Accordingly, it is desired to impart a further potent antibody producing ability to the mucosal vaccine.

An object of the invention is to provide an improved mucosal vaccine having a more potent ability in antibody producing than those of mucosal vaccines described in Patent Documents 3, and, as a result, being capable of exerting an excellent effect comparable to a subcutaneously injectable vaccine, even with an extremely small amount of an antigen.

Means for Solving the Problems

The inventors, as a means for further enhancing the antibody induction ability of the mucosal vaccines of Patent Documents 3, examined gelators (CVP, HPC) employed in a nasal drop or a mucosally applicable vaccine whether they can function in AD vehicle to increase the amount of the antigen to be delivered to an antigen presenting cell by nasal-clearance prolongation and thereby inducing a mucosal immune IgA and a blood immune IgG, and the followings were confirmed.

(1) When compared with the mucosal vaccines (antigen+synthetic peptide+lipids) in Patent Document 3 or the mucosal vaccines (antigen+CVP) in Patent Documents 5 and 6, a mucosal vaccine consisting of "antigen+synthetic peptide+lipid+CVP" has a far more excellent antibody inducing ability, and its effect far exceeds the scope predicted from a simple combination of Patent Document 3 (antigen+synthetic peptide+lipids) and Patent Documents 5 and 6 (antigen+CVP).
(2) An excipient, HPC, known widely as a gelator for a nasal drop or a mucosal vaccine similarly to CVP, has no antibody inducing ability, and can not be expected to exert a mucosal IgA- and blood IgG-inducing effect when used with an antigen as well as with an antigen and an AD vehicle.
(3) Even when reducing the amount of the antigen to about ⅕ or less of the amount required in the mucosal vaccine (antigen+synthetic peptide+lipids) in Patent Document 3, the "antigen+synthetic peptide+lipids+CVP" mucosal vaccine has a far more potent antibody inducing effect.

The invention was established based on the novel findings above.

Accordingly, the invention is a mucosal vaccine producing an antigen-specific mucosal IgA and blood IgG in the levels capable of exerting an effective immune induction and an infection-preventing effect, which comprises:

(a) an AD vehicle consisting of a synthetic peptide and a lipid(s), wherein the synthetic peptide consisting of the amino acid sequence KnLm (wherein n is 4 to 8 and m is 11 to 20);
(b) a carboxyvinyl polymer; and,
(c) an antigenic protein, in an amount incapable of producing a sufficient mucosal IgA and blood IgG for exerting an effective immune induction and an infection-preventing effect when used by itself.

In the mucosal vaccine of the present invention, the antigen protein (c) is in an amount, even in combination with the AD vehicle (a) or in combination with the carboxyvinyl polymer (b), incapable of producing an antigen-specific mucosal IgA and blood IgG sufficient for exerting an effective immune induction and an infection-preventing effect.

In one aspect of this mucosal vaccine, the synthetic peptide consists of the amino acid sequence of SEQ ID NO: 1 or 2.

In another aspect of this mucosal vaccine, the lipid is at least one of phosphatidyl choline, dipalmitoylphosphatidyl choline, phosphatidyl serine, phosphatidyl glycerol, phosphatidyl inositol, phosphatidyl ethanolamine, phosphatidic acid, lauric acid, myristic acid, palmitic acid, stearic acid and oleic acid. More specifically, the lipids are a mixture of dipalmitoylphosphatidyl choline, phosphatidyl glycerol and palmitic acid.

In a further aspect of this mucosal vaccine, the antigen is a pathogen-derived inactivated antigen, a purified antigen, a partially purified antigen, a recombinant antigen, a detoxicated toxin, or an allergen causative of an allergy.

The present invention is also a method for producing a mucosal vaccine producing an antigen-specific mucosal IgA and blood IgG in the levels capable of exerting an effective immune induction and an infection-preventing effect, which comprises:
(a) an AD vehicle consisting of a synthetic peptide and a lipid(s), wherein the synthetic peptide consisting of the amino acid sequence KnLm (wherein n is 4 to 8 and m is 11 to 20);
(b) a carboxyvinyl polymer; and,
(c) an antigenic protein, in an amount incapable of producing a sufficient mucosal IgA and blood IgG for exerting an effective immune induction and an infection-preventing effect when used by itself, which method comprises:
(1) suspending said (a) and (c) in water;
(2) repeating warming and stirring once or more;
(3) freezing and lyophilizing,
(4) suspending the lyophilized form in physiological saline to adjust to a predetermined concentration; and,
(5) adding a solution of said (b).

As used herein, the phrase "amounts of a mucosal IgA and a blood IgG capable of exerting an effective immune induction" mans any amounts of IgA and IgG such that give the hemagglutination inhibition (HI) values of blood not lower than the international evaluation criteria.

In the following description, a composition consisting of a synthetic peptide and lipids may be referred to as an "AD vehicle", and a composition consisting of the AD vehicle and an antigen may be referred to as a "mucosal vaccine". These "AD vehicle" and "mucosal vaccine" are identical substantially to those disclosed in Patent Document 3. In addition, a composition of the mucosal vaccine combined with a CVP may be referred to as a "CVP-added mucosal vaccine". In this invention, the "lipids" encompasses the disclosures of Patent Documents 1 to 3, and the "synthetic peptide" and the "AD vehicle" encompasses the disclosure of Patent Document 3.

Effects of the Invention

The CVP-added mucosal vaccine of the present invention has an extremely high vaccine antigen-specific IgA and IgG antibody inducing effect and a potent hemagglutination inhibition (HI) effect of the induced antibody, which far exceeds the international protective standard. These effects are extremely marked also when compared with the mucosal vaccines described in Patent Document 3 or the "vaccine antigen+CVP" (Patent Documents 5 and 6), and are excellent effects which can not be predicted from the mucosal vaccine effect of Patent Document 3 or the CVP effect of Patent Documents 5 and 6.

Due to such a potent antibody inducing ability, a required preventative effect can be accomplished even when the antigen is contained only in an amount smaller than that of a conventional mucosal vaccine. Thus, the CVP-added mucosal vaccine of the invention can exert a far potent antibody inducing effect even when the amount of the antigen employed is reduced to ⅕ or less then the amount in a conventional mucosal vaccine (antigen+synthetic peptide+lipids). For example, as shown in Experiment 2, the mucosal vaccine of Patent Document 3, using an influenza antigen as an antigen, shows a hemagglutination inhibition (HI) value less than HI=40, which is an international evaluation criteria of an influenza vaccine, even when the antigen amount is 0.2 μg, while the CVP-added mucosal vaccine of the invention exhibits an excellent protective immunity effect reflected by HI values of 100 or more even with an antigen amount of 0.1 μg or 0.03 μg.

In addition, the composition itself (AD vehicle, CVP) of the CVP-added mucosal vaccine of the invention has no effect for stimulating antigen recognizing cells, and accordingly it has an extremely low possibility of developing an unexpected side effect such as autoimmune diseases or post-vaccination allergy exacerbation due to any antigens other than the vaccine antigen.

Also according to the method for producing a mucosal vaccine of the invention, a mucosal vaccine having a further higher ability of producing the antigen-specific mucosal IgA and blood IgG can be produced.

MODE FOR CARRYING OUT THE INVENTION

Figure 1:
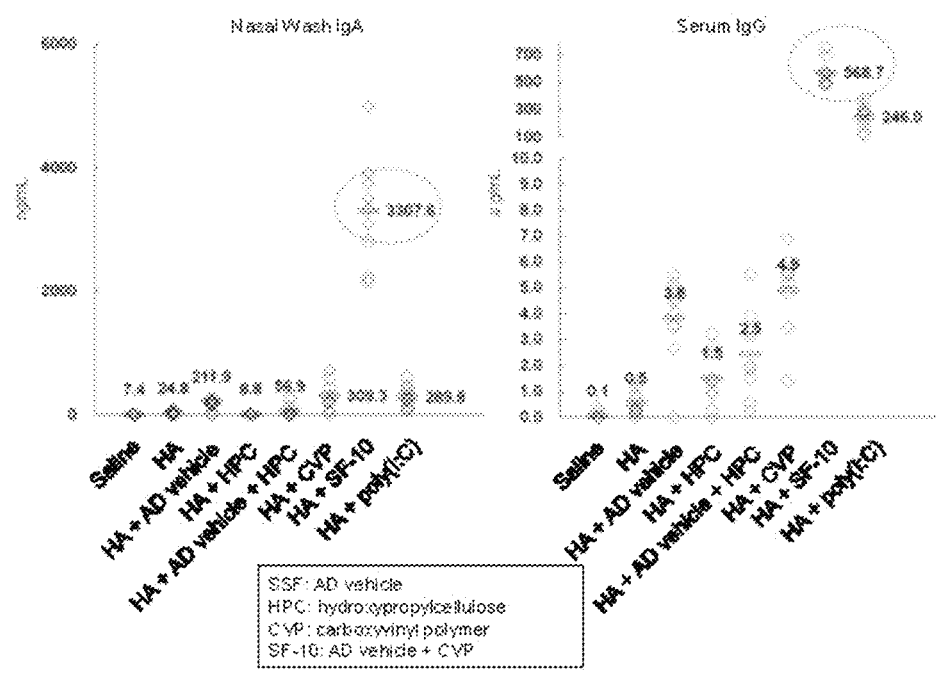
FIG. 1 The results of Experiment 1, which indicate the nasal wash IgA levels (left) and serum IgG levels (right) when mice are treated nasally with either of the vaccines of Example 1 and Comparative Examples 1 to 5 or an HA antigen.

The CVP-added mucosal vaccine of the invention consists of the following composition.

Synthetic Peptide

A synthetic peptide consists of the amino acid sequence of KnLm (wherein n is 4 to 8, and m is 11 to 20). KnLm has n×K(Lys) residues on the N-terminus side and m×L residues on the C-terminus side. Such a synthetic peptide may be any of the following peptides. In the parenthesis, the abbreviation of a peptide is indicated. The amino acid residue is indicated as a single letter code.

```
SEQ ID NO: 1(K6L16):    KKKKKKLLLLLLLLLLLLLLLL

SEQ ID NO: 2(K6L11):    KKKKKKLLLLLLLLLLL
```

SEQ ID NO: 1 (K6L16) consists of 6 K(Lys) residues on the N-terminus side and 16 L residues on the C-terminus side, and SEQ ID NO: 2 (K6L11) consists of 6 K(Lys) residues on the N-terminus side and 11 L residues on the C-terminus side. These synthetic peptides should be those prepared according to known chemical synthesis methods whose purities are 95% or higher.

Lipid

A phospholipid contained in a pulmonary surfactant, such as phosphatidyl choline, dipalmitoylphosphatidyl choline, phosphatidyl serine and phosphatidyl glycerol is employed preferably. Otherwise, phosphatidyl inositol, phosphatidyl ethanolamine, phosphatidic acid, sphingomyelin, and the like may also be employed. As fatty acids, lauric acid, myristic acid, palmitic acid, stearic acid, palmitooleic acid, oleic acid, and the like may be employed. It is also possible to employ a lipid derived from aquatic animals such as whale and dolphin whose lungs are inflated dynamically.

Carboxyvinyl Polymer (CVP)

The CVP is a hydrophilic polymer obtained by polymerizing acrylic acid as a main component, and commercially available ones such as Hivis Wako 103, Hivis Wako 104, Hivis Wako 105, Sigma Corporation's product pAA130 (Sigma, St. Louis, Mo., Cat No. 181293), pAA450 (Sigma, Cat No.181285) and pAA1250 (Sigma, Cat No.306215) can be employed. Among these, Hivis Wako 104, and Sigma Corporation's products pAA130 and pAA1250 which are employed widely in producing cosmetic and pharmaceutical gels are preferred. After producing a 0.2 to 2.0% by weight solution of CVP in pure water or physiological saline under ultrasonic treatment, a NaOH neutralizing solution can be employed to adjust to pH5.0 to 10.5, while it is preferred to employ a pH by which the stability of the vaccine antigen is not affected adversely. For example, an influenza split vaccine antigen is adjusted to pH6.8 to 8.0, preferably pH7.0 to 7.2.

Antigen

The antigen includes antigen molecules such as a highly purified bacterial antigen for vaccination whose purity is about 90% or higher, a viral antigen, a protein such as a toxoid, a glycoprotein, an allergen, a polymeric saccharide and a nucleic acid. For example, the antigen for a vaccine against a chickenpox virus, a measles virus, a mumps virus, a poliovirus, a rotavirus, an influenza virus, an adenovirus, a herpes virus, a severe acute respiratory infection syndrome (SARS) virus, a West Nile virus, a Hantaan virus, a dengue virus, a Japanese encephalitis virus, a yellow fever virus, a tick-borne encephalitis virus, an HIV virus, a hepatitis C virus, a *Bordetella pertussis*, a meningococcus, an influenza B, a Pneumovirus, a *Vibriocholera*, a *Plasmodium*, a sleeping sickness pathogen and the like is contemplated.

The antigen is employed in the amount, when used alone, or especially when combined with AD vehicle (a) or combined with a carboxyvinyl polymer (CVP), which is adjusted so that the antigen-specific mucosal IgA and blood IgG in an amount producing an effective immune induction is not produced.

The influenza antigenic protein contains a protein M, a neuraminase, a nucleoprotein and the like in addition to HA antigen molecule. In the following description, the antigenic protein amount means a total protein amount including the antigenic molecules listed above. The amount of HA antigen molecule itself was about 50% of the total antigenic protein in the case of the influenza vaccine of the lot employed.

The followings are the description of the method for preparing an AD-vehicle and a CVP-added mucosal vaccine from the materials described above.

AD Vehicle Preparation

Several lipids from those listed above are mixed in a suitable ratio and suspended in a chloroform: methanol (2:1

(v/v)) mixture for example at a concentration as a lipid of 10 mg/mL, and employed as a lipid component. The synthetic peptide is dissolved in ethanol for example at a concentration of 5.0 mg/mL. Then these lipid component and synthetic peptide are mixed. The mixing ratio involves about 0.2 to about 12.0% by dry weight for the synthetic peptide, and about 88 to about 99.8% by dry weight for the lipid. This mixture is evaporated into dryness at about 40° C. using a rotary evaporator and resuspended in 10% ethanol at a suitable concentration, stirred and mixed for about 15 minutes in a water bath at about 45° C. to yield a uniform dispersion, which is then freezed and dried. This dried substance is stored at about −30° C., and at every time of use it is suspended with pure water or physiological saline, and then subjected to an ultrasonic wave, a homogenizer, a mixer, a stirrer and the like, to form a uniform dispersion.

CVP-added Mucosal Vaccine Preparation

The aforementioned AD vehicle, CVP and antigen are mixed in a suitable ratio. Thus, in the case of an influenza vaccine, the AD vehicle solution is admixed in the vaccine stock solution so that the ratio of the AD vehicle amount (V) to the antigenic protein (A) on the dry weight basis, i.e. V/A, becomes a desired value. The dry weight of the antigenic protein (A) to be administered to a single mouse is about 0.01 to about 10 pg/kg body weight, preferably about 0.03 to about 5.0 μg/kg body weight. This antigenic protein amount is ⅕ or less of the antigen amount (about 0.1 to about 50 μg/kg body weight, preferably about 0.3 to about 30 μg/kg body weight) in the mucosal vaccine of Patent Document 3 (antigen+AD vehicle).

In such an antigen amount, the V/A for inducing the IgA antibody production predominantly and selectively is preferably about 0.1 to about 1.0. On the other hand, the V/A for inducing the production of both of the IgA and IgG antibodies is about 1.0 to about 100, preferably about 5 to about 20. In the V/A described above, about 60% or more of the antigen is bound to the AD vehicle, and the resultant mucosal immune vaccine is capable of inducing the IgA antibody production and/or the IgG antibody production efficiently.

The CVP concentration of the final nasal vaccine solution to which CVP was added is about 0.1% to 1.0%, preferably 0.3% to 0.8%. The AD vehicle, the antigen and CVP can be mixed uniformly using a homogenizer, a mixer, an agitator, a stirrer and the like.

Typically, as shown in Example 1 described below, the antigenic protein and the AD vehicle are mixed, and then subjected to an ultrasonic treatment for 3 minutes, and then vortexed for 2 hours at room temperature, and finally combined with an equal volume of a 1% CVP solution in physiological saline, thereby producing the CVP-added mucosal vaccine. This method is identical to the method described in Patent Document 3 except for adding CVP. Nevertheless, this method is disadvantageous since it may allow the viral antigen to become inactivated due to the heat generated by the ultrasonic treatment and the ultrasonic treatment process poses a difficulty in keeping a constant condition in view of the type of the instrument employed, the size of the oscillator, the state of the oscillator and the like.

Accordingly, a production method exemplified in Example 7 is preferred, which method comprises the following steps:
(1) suspending the AD vehicle and the antigenic protein in water (pure water);
(2) repeating warming and stirring once or more;
(3) freezing and lyophilizing,
(4) suspending the lyophilized samples in physiological saline to adjust to a predetermined concentration; and,
(5) adding the CVP solution dissolved in physiological saline.

This is an excellent method serving not only to solve the aforementioned problems associated with the ultrasonic treatment but also to enable a further enhanced production of the antigen-specific IgA and IgG.

The CVP-added mucosal vaccine thus prepared may be used in a single dosing, but it is used preferably in two dosings (initial immunization and secondary immunization) or three dosings (initial immunization, secondary immunization and tertiary immunization). Such a repeated immunizing treatment allows the antibody titres of antigen-specific IgA and IgG to be increased markedly. The two or three vaccine dosings are conducted at intervals of 1 week to 3 weeks, preferably about 2 weeks. The administration of the CVP-added mucosal vaccine of the invention can be done to the nasal cavity as well as the oral cavity or the vaginal cavity (see for example Lubrizol Pharmaceutical Bulletin, Polymers for Pharmaceutical Applications, Lubrizol Advanced Materials, Inc. 2008).

The present invention is further detailed typically in the following Examples but the invention is not limited to the following examples.

EXAMPLE 1

[Manufacturing Steps Involving Ultrasonic Treatment]

An AD vehicle was prepared as described below. Dipalmitoylphosphatidylcholine (DPPC), phosphatidyl glycerol (PG) and palmitic acid (PA) were mixed in a ratio of 75:25:10 (w/w/w) and suspended in a chloroform:methanol (2:1 (v/v)) mixture solution at a concentration as a phospholipid of 10 mg/ml to obtain a lipid component. A synthetic peptide K6L16 (KKKKK-KLLLLLLLLLLLLLLLLL)(product of GenScript Inc.) having a purity of 95% or higher was dissolved in methanol at 5.0 mg/mL. The lipid component (DPPC:PG:PA=75:25:10, w/w/w) solution and the K6L16 peptide solution were mixed in a weight ratio of the phospholipid component: K6L16=100: 2 and evaporated into dryness at 40° C. using a rotary evaporator. This was resuspended in 10% ethanol at a concentration as a phospholipid of 4 mg/ml, stirred and mixed for about 15 minutes in a water bath at about 45° C. to yield a uniform dispersion. This was freezed and dried, and then stored as an AD vehicle at −30° C.

Then, the aforementioned AD vehicle was employed to prepare a CVP-added mucosal vaccine as described below.

The freeze dried AD vehicle was used as being suspended in physiological saline just before use. The influenza vaccine (HA) antigen employed was A/NewCaledonia/20/99(H1N1) provided by The Research Foundation for Microbial Diseases of Osaka University at 1.94 mg protein/mL (sodium phosphate buffer solution, sodium chloride, thimerosal solution: containing, per ml, 3.53 mg of sodium hydrogen phosphate hydrate, 0.54 mg of sodium dihydrogen phosphate, 8.50 mg of sodium chloride and 0.008 mg of thimerosal). The vaccine and the AD vehicle were mixed in such a ratio that the ratio of the antigen solution protein amount (A) to the AD vehicle solution phospholipid amount (V), i.e. VA=10, subjected to an ultrasonic treatment involving On and OFF three times repetitively at intervals of 30 seconds to accomplish the ultrasonic treatment for 3 minutes in total including ON for 90 seconds and OFF for 90 seconds in total (model S-250D, Branson Ultrasonics Danbury), then vortexed for 2 hours at room temperature and dissolved in physiological saline, and then combined with a neutralized 1% CVP (Hivis Wako 104) at a final concentration of 0.5%. Thus, the composition contained in 4 pl in total to be administered into the both nasal cavities of a single mouse with 2 μl being given to each nostril is the influenza vaccine (HA) antigen protein amount/AD vehicle solution's phospholipid amount/CVP weight =0.2 μg/2.0 μg /20 μg. The pH of this CVP-added mucosal vaccine was within the range for allowing the antigenicity of the HA antigenic protein to be maintained (7.0 to 7.2).

Hereinafter the CVP-added mucosal vaccine was designated as "HA+SF-10". While the SF-10 amount is AD vehicle (2.0 μg)+CVP (20 μg)=22 pg as described above, the following description employs the designation SF-10 (2.0 μg) to represent the amount of the AD vehicle phospholipid which serves as a basis for the vehicle effect of the adjuvant. The SF-10 amounts in other Examples are indicated as values excluding the CVP amounts.

EXAMPLE 2

According to the method in Example 1, a CVP-added mucosal vaccine of which HA antigenic protein amount was 0.1 μg was prepared. The mixing ratio of the HA antigenic protein, the AD vehicle and CVP was identical to that in Example 1 (i.e., containing the AD vehicle in an amount 10 times the antigenic protein amount and CVP at a final concentration of 0.5%).

EXAMPLE 3

According to the method in Example 1, a CVP-added mucosal vaccine of which HA antigenic protein amount was 0.03 μg was prepared. The mixing ratio of the HA antigenic protein, the AD vehicle and CVP was identical to that in Example 1 (i.e., containing the AD vehicle in an amount 10 times the antigenic protein amount and CVP at a final concentration of 0.5%).

COMPARATIVE EXAMPLE 1

The mucosal vaccine of Patent Document 3 (HA+AD vehicle) was prepared. The HA antigenic protein and the AD vehicle were identical to those in Example 1, and the preparation of the vaccine was conducted as same to Example 1. The HA antigenic protein amount was 0.2 μg and the AD vehicle amount was 2.0 μg.

COMPARATIVE EXAMPLE 2

The mucosal vaccine disclosed in Patent Documents 5 and 6 (HA+CVP) was prepared. The HA antigenic protein and CVP were identical to those in Example 1, and the preparation of the vaccine was conducted as same to Example 1. The HA antigenic protein amount was 0.2 μg and the final concentration of CVP was 0.5%

COMPARATIVE EXAMPLE 3

The mucosal vaccine disclosed in Patent Document 4 (HA+HPC) was prepared. The HA antigenic protein was identical to that in Example 1, and HPC was a commercially available HPC 6.0-10.0 (Wako Pure Chemical Industries, Ltd.) The preparation of the vaccine was conducted as same to Example 1. The HA antigenic protein amount was 0.2 μg and the HPC amount was 20 μg.

COMPARATIVE EXAMPLE 4

A mucosal vaccine (HA+AD vehicle+HPC) was prepared by combining the HA+AD vehicle of Patent Documents 3 with HPC. The HA+AD vehicle was identical to that in Comparative Example 1 and HPC was identical to that in Comparative Example 3, while the preparation of the vaccine was conducted as same to Example 1. The HA antigenic protein amount was 0.2 μg, the AD vehicle amount was 2.0 μg, and the HPC amount was 20 μg.

COMPARATIVE EXAMPLE 5

A mucosal vaccine (HA+poly (I:C)) containing a poly (I:C) (Alexis Corp.) which is a ligand of a Toll-Like Receptor (TLR) of a dendritic cell and which stimulates an antigen presenting cell strongly to promote the antibody production was prepared in accordance with the method described in a publication (Asahi-Ozaki Y et al., Microbes Infect 2006; 8:2706-2714, Ichinohe T, et al., J Virol 2005; 79(5): 2910-2919). The HA antigenic protein amount is 0.2 μg and the poly (I:C) amount is 2 μg.

COMPARATIVE EXAMPLE 6

The HA antigen was diluted with physiological saline and employed as a vaccine. The HA antigenic protein dose per animal was 0.2 μg.

EXPERIMENT 1

Using mice, the antibody production enhancing effects of the nasal mucosal vaccines were tested.
1. Mucosal Vaccine
   HA+SF-10 (Example 1)
   HA+AD Vehicle (Comparative Example 1)
   HA+CVP (Comparative Example 2)
   HA+HPC (Comparative Example 3)
   HA+AD Vehicle+HPC (Comparative Example 4)
   HA+poly (I:C) (Comparative Example 5)
   HA Alone (Comparative Example 6)
2. Animals
   Female BALB/c mice (6-8 week-old) purchased from Japan SLC, Inc. (Shizuoka, Japan) were used. All animal experiments were conducted in an infected animal building (level P2) in Institute for Animal Experimentation, The University of Tokushima, School of Medicine, in accordance with the guidelines of Committee for Animal Experimentation of University of Tokushima, School of Medicine.
3. Immunization Method
   In administering the vaccine nasally, 2 μl of 5 mucosal vaccines described in above Section 1 was respectively administered to each nostril, thereby instillating 4 μl in total to the both nasal cavities of each mouse under anesthesia with Ketalar (62.6 mg/kg) and Selactar (12.4 mg/kg). As controls, groups treated with physiological saline and Comparative Example 6 (HA antigenic protein alone) in an amount identical to that of the vaccine solution were employed. Each group consisted of 9 to 10 mice.
   The secondary boost immunization was conducted by the nasal administration of the identical dose of vaccines at two weeks after the initial immunization. After the secondary immunization for two weeks, the tertiary immunization was conducted by a similar method, and at two weeks after last immunization the samples were taken. While the vaccine was given three times in total, the secondary immunization as the final immunization can give almost similar results.

4. Preparation of Mouse Nasal Cavity and Alveolar Washes

At two weeks after the tertiary immunization, nasal cavity/alveolar washes and serum were prepared for measurements of the viral HA antigen-specific IgA and IgG. The procedures were same to the description of a publication (Mizuno D, Ide-Kurihara M, Ichinomiya T, Kubo I, Kido H. Modified pulmonary surfactant is a potent adjuvant that stimulates the mucosal IgA production in response to the influenza virus antigen. J Immunol. 2006;176:1122-30).

A vaccine-treated mouse was anesthetized with pentobarbital to a thoracolaparotomy, and the tracheal duct was incised to insert an Atom venous catheter 3 Fr having nodes (Atom Medical Corporation, Tokyo, Japan) into the lung, to which then 1 mL of physiological saline was infused and then recovered. This procedure was repeated three times and the resultant 3 mL in total was employed as an alveolar wash. After collecting the alveolar wash, an Atom venous catheter was inserted via the incised tracheal duct to the direction of the nasal cavity, to which 1 mL of the physiological saline was infused and the fluids coming out of the nose were collected. The fluids were employed as nasal washes. In addition, a blood was taken out from the heart, centrifuged for 10 minutes at 5000 rpm to prepare a serum.

5. Quantification of Anti-Influenza Antibody

The anti-influenza-specific IgA and IgG levels in the nasal cavity/alveolar washes and serum were quantified by ELISA assay, according to the description of the aforementioned publication (Mizuno D, et al. J Immunol. 2006; 176:1122-30).

ELISA assay was conducted according to the method for a Mouse ELISA quantitation kit of BETHYL LABORATORIES, INC. (Texas, United States). To each well of a 96-well Nunc immunoplate (Nalgen Nunc International, New York, United States), 1 μg of the vaccine and 100 μL of a 1 μg/mL PBS solution of bovine serum albumin (BSA, SIGMA, Missouri, United States) were added, and allowed to undergo a solid phase immobilization reaction overnight at 4° C. Thereafter, the vaccine fluid was removed by washing three times with a washing fluid (50 mM Tris, 0.14 M NaCl, 0.05% Tween 20, pH 8.0). To each well, 200 μL of a 50 mM Tris-HCl buffer solution (pH8.0) containing 0.15 M NaCl and 1% BSA was added, and a blocking reaction was conducted for 1 hour at room temperature. After washing each well three times with the washing fluid, 100 μL of the nasal washes, the pulmonary washes or the sera, which were diluted suitably with a sample binding buffer solution (50 mM Tris, 0.15 M NaCl, 1% BSA, 0.05% Tween 20, pH 8.0), were added, and reacted for 2 hours at room temperature. A goat anti-mouse IgA or IgG-horse radish peroxidase (HRP) (BETHYL LABORATORIES INC.) was employed as a secondary antibody, and a TMB Microwell Peroxidase Substrate System (Kirkegaard & Perry Laboratories, Inc. Maryland, United States) was employed to conduct a chromogenic reaction. The reaction was terminated by adding 100 μL of a 2 M $H_2SO_4$ (Wako Pure Chemical Industries, Ltd.) to each well, and the absorbance at 450 nm was measured using SPECTRAmax PLUS 384. As a standard for the quantification, the absorbance obtained similarly using 10 ng of the anti-influenza IgA and IgG purified from the aforementioned pulmonary washing was employed.

6. Results

Figure 2:
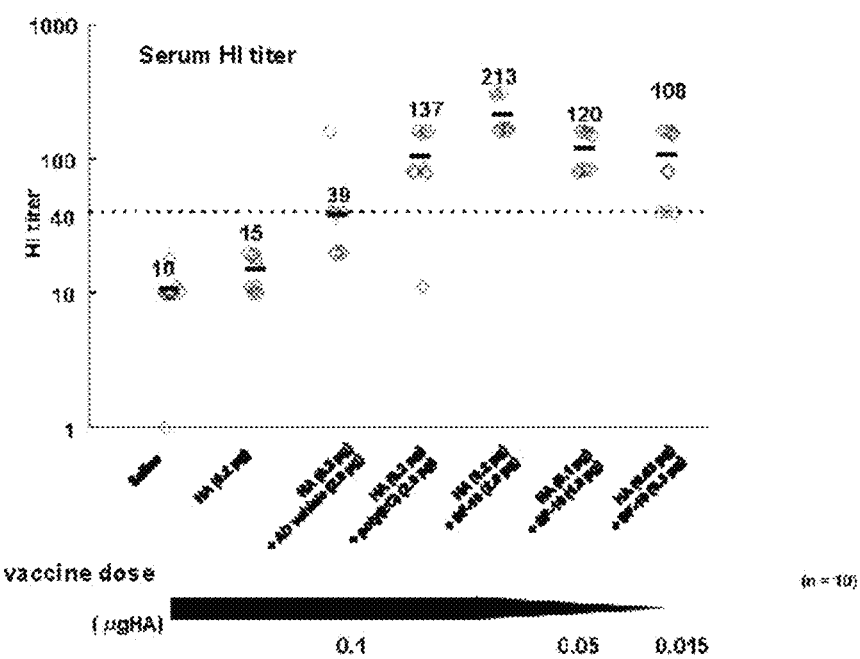
FIG. 2 The results of Experiment 1, which indicate the HI values exhibited by an anti-influenza virus HA antibody when mice are treated nasally with either of the vaccines of Example 1 and Comparative Examples 1 and 5, HA antigen or HA+AD vehicle as a reference control.

The results of the anti-influenza HA antibody induction are shown for the IgA in the nasal washes (FIG. 1, left) and for the IgG in the blood (FIG. 1, right). The respective measured values are shown in Table 1. FIG. 2 and Table 2 show the HI titers of the respective test groups.

(1) The group treated only with the HA antigen (Comparative Example 6) exhibited an antigen-specific IgA level of 24.77 ng/mL and IgG level of 0.54 μg/mL, while the HA+SF-10 (Example 1) treatment group exhibited an antigen-specific IgA level of 3307.60 ng/mL and IgG level of 568.75 μg/mL, showing 132-fold enhancement for the IgA in the nasal washes and 1137-fold enhancement for the IgG in the sera. It was confirmed that the CVP-added mucosal vaccine (HA+SF-10) of the present invention has an extremely potent antibody inducing effect (FIG. 1, Table 1).

(2) The antibody production in the HA+SF-10 (Example 1) treatment group was greater by 15.6 times for the antigen-specific IgA and by 150 times for the IgG when compared with the HA+AD vehicle (Comparative Example 1) and greater by 10.7 times for the antigen-specific IgA and by 115.4 times for the IgG when compared with the HA+CVP (Comparative Example 2) (FIG. 1, Table 1). Such a remarkably excellent antibody inducing effects with the HA+SF-10 far exceeded the scope predicted from a simple combination of the known mucosal vaccine (HA+AD vehicle) of Patent Document and the known CVP of Patent Documents 5 and 6.

(3) The antibody production by the HA+HPC (Comparative Example 3) treatment group was similar to or less than that in the group treated only with HA (Comparative Example 6). The antibody production by the HA+AD vehicle+HPC (Comparative Example 4) treatment group was lower than that in the HA+AD vehicle (Comparative Example 1) group (FIG. 1, Table 1). Based on these results, HPC, which is known widely as a gelator in a nasal drop formulation or a mucosal vaccine additive similarly to CVP, was confirmed to have no immune induction enhancing effect when used in combination with the antigen and the AD vehicle. Accordingly, the enhancement by additive CVP of the adjuvant effect of the AD vehicle is assumed to be attributable to the nature of AD vehicle rather than a simple effect to increase the viscosity of vaccine.

(4) The antibody production in the HA+SF-10 (Example 1) treatment group was greater by 11.4 times for the IgA in the nasal washes and by 2.3 times for the IgG in the sera when compared with the HA+poly (I:C) (Comparative Example 5) (FIG. 1, Table 1). Based on these results, the CVP-added mucosal vaccine (HA+SF-10) of the invention was confirmed to have a more potent immune induction effect than poly (I:C) which stimulates antigen presenting cells potently to promote the antigen production.

TABLE 1

| | Antibody titre | | | | | |
|---|---|---|---|---|---|---|
| | nasal wash IgA (ng/mL) | | | serum IgG(μg/mL) | | |
| | mean | S.D. | S.E. | mean | S.D. | S.E. |
| Physiological saline | 7.45 | 4.79 | 1.51 | 0.06 | 0.14 | 0.04 |
| HA | 24.77 | 25.83 | 8.17 | 0.54 | 0.48 | 0.15 |
| HA + AD vehicle | 211.94 | 167.90 | 53.10 | 3.84 | 0.91 | 0.29 |
| HA + HPC | 8.82 | 4.96 | 1.65 | 1.51 | 1.12 | 0.37 |
| HA + AD vehicle + HPC | 56.92 | 89.05 | 29.68 | 2.46 | 1.67 | 0.56 |
| HA + CVP | 309.34 | 231.08 | 77.03 | 4.93 | 1.61 | 0.54 |
| HA + SF-10 | 3307.60 | 882.55 | 294.18 | 568.75 | 95.18 | 31.73 |
| HA + poly(I:C) | 289.78 | 136.40 | 43.13 | 246.04 | 90.93 | 28.76 |

(5) While under the international evaluation criteria of the influenza vaccine for protective immunity in which a vaccine exceeding the hemagglutination inhibition (HI) titer≥40 is judged as effective, only 50% of the samples in the HA+AD vehicle (Comparative Example 1) exceeded HI≥40, with the mean value of HI=39. On the contrary, the HA+SF-10 (Example 1) showed HI>40 in all the samples, and the mean value was as high as HI=213.3, and exhibited a potent viral protective effect, which was 1.56 times of that by the HA+poly (I:C) (Comparative Example 5), which showed HI=137.0 (FIG. 2, Table 2).

TABLE 2

| | HI titer | | |
|---|---|---|---|
| | mean | S.D. | S.E. |
| Physiological saline | 10.6 | 6.60 | 2.09 |
| HA | 15.3 | 5.91 | 1.87 |
| HA + SSF | 39.0 | 30.35 | 9.60 |
| HA + SF-10 | 213.3 | 80.00 | 26.67 |
| HA + poly(I:C) | 137.0 | 105.63 | 33.40 |

EXPERIMENT 2

A antigen presenting dendritic cells prepared by the method of publication (Mizuno D et al., J Immunol 2006; 176:1122-1130) was stimulated with each of an endotoxin (LPS: 100 ng/1×$10^5$ cells) (Grauer O, et al., Histochem Cell Biol 2002; 117:351-362), poly(I:C) (10 μg/1×$10^5$ cells) and SF-10 (CVP-added AD vehicle 10 μg/1×$10^5$ cells), and the expression levels of the cell membrane activation marker molecules (MHC II, CD40, CD80(B7-1) and CD86(B7-2)) were measured.

Figure 3:
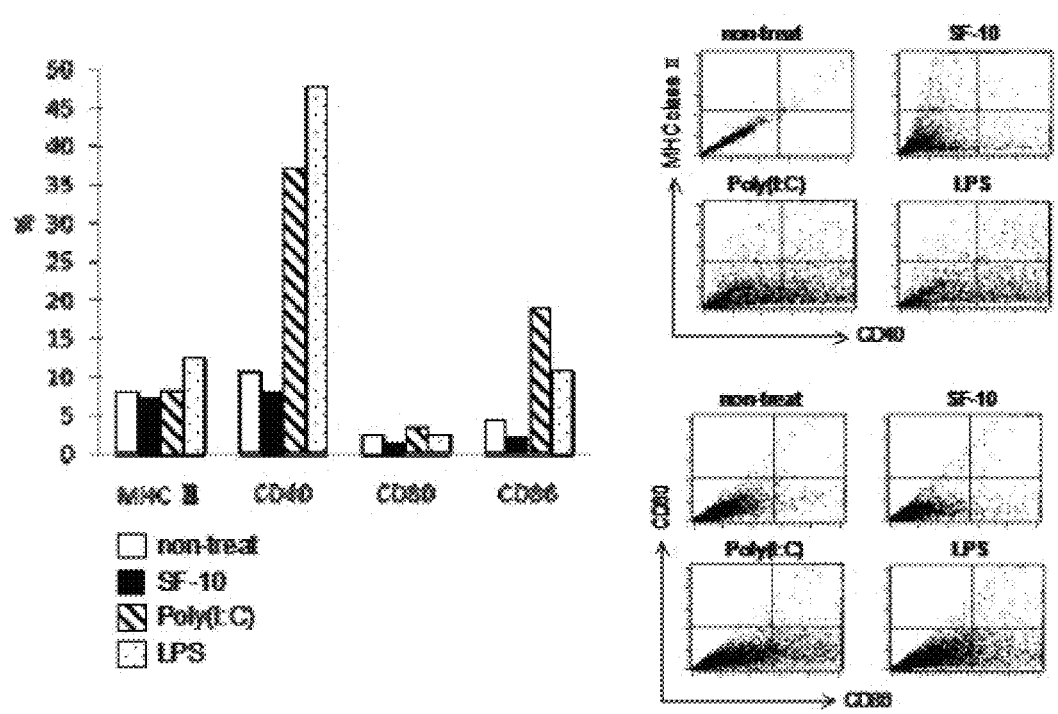
FIG. 3 The results of Experiment 2, which indicate the change in expression levels of activation marker molecules (MHC II, CD40, CD80(B7-1) and CD86(B7-2)) on the cell membrane, when antigen-presenting dendritic cells are stimulated with endotoxin (LPS), poly(I:C) and SF-10 (CVP+AD vehicle) respectively. The left graph shows the ratio (%) of the positive cells in the total cell count, which indicates an increased expression of each membrane molecule (the cells show over the negative cut off value limit as indicating bar near the center, which was determined based on the saline treatment employed as a control in the dot graphs on the right). The right shows the results of flow cytometry measurement, in which the amount of the activation marker molecules on the cell membrane is visualized.

The results are shown in FIG. 3. LPS and poly (I:C) increased the expression of CD40 and CD86 markedly and activated the antigen presenting dendritic cells, while SF-10 itself did not increase the expression of MHC II, CD40, CD80 and CD86 on the antigen presenting dendritic cells, showing a level almost equal to the expression in the control (non-treatment cell).

Based on these results, it was assumed that SF-10 did not directly stimulated the antigen presenting dendritic cells without antigen, i.e., SF-10 stimulates the antigen delivery effectively to the antigen presenting dendritic cells thereby inducing the antibody production.

EXPERIMENT 3

Each CVP-added mucosal vaccine of Example 1 (HA antigenic protein amount: 0.2 μg), Example 2 (HA antigenic protein amount: 0.1 μg) and Example 3 (HA antigenic protein amount: 0.03 μg) was administered to mice (10 animals in each group) similarly to Experiment 1, and the IgA in the antigen-specific nasal washes and the IgG in the blood were measured similarly to Experiment 1.

The results are shown in Table 3. Example 1 (HA antigenic protein amount: 0.2 μg) and Example 2 (HA antigenic protein amount: 0.1 μg) exhibited almost equal antibody inducing effect. Moreover, Example 3 (HA antigenic protein amount: 0.03 μg) whose antigenic protein amount is ⅙ or less of that in Example 1 also exhibited a far potent antibody inducing effect when compared with Comparative Example 2: HA+AD vehicle (HA antigenic protein amount: 0.2 μg) and Comparative Example 3: HA+CVP (HA antigenic protein amount: 0.2 μg) in Experiment 1 (Table 1). Thus, the Example 3 treatment group exhibited an antigen-specific IgA level which was 11.7 times of that in Comparative Example 2 and 8.0 times of that in Comparative Example 3, and an IgG amount which was 77.2 times of that in Comparative Example 2 and 60.1 times of that in Comparative Example 3.

Based on these results, the CVP-added mucosal vaccine of the invention was confirmed to be capable of producing a sufficient amount of the antibody with the antigen in an amount far less than those in the mucosal vaccines of Patent Document 3 (HA+AD vehicle) and Patent Documents 5 and 6 (HA+CVP). Also with regard to the hemagglutination inhibition effect (HI effect), the CVP-added mucosal vaccine exhibited a sufficient protective effects realized by HI=198.0 even with an HA antigenic protein amount of 0.03 μg.

TABLE 3

| Change in concentration of HA antigen in CVP-added vaccine (HA + SF-10) and anti-influenza antibody inducing effect in nasal wash and blood | | | | | | | | | |
|---|---|---|---|---|---|---|---|---|---|
| HA + SF-10 | Nasal wash IgA (ng/mL) | | | Serum IgG (μg/mL) | | | Serum HI titer | | |
| HA protein dose (μg/head) | mean | S.D. | S.E. | mean | S.D. | S.E. | mean | S.D. | S.E. |
| HA = 0 | 7.30 | 4.21 | 1.12 | 0.06 | 0.11 | 0.03 | 5.8 | 6.12 | 1.89 |
| HA = 0.03 | 2480.41 | 651.24 | 223.11 | 296.32 | 83.43 | 27.58 | 198.0 | 80.36 | 23.32 |
| HA = 0.10 | 3100.22 | 781.13 | 263.36 | 588.61 | 94.30 | 30.42 | 220.0 | 82.73 | 29.27 |
| HA = 0.20 | 3200.18 | 803.45 | 291.10 | 550.60 | 93.10 | 29.31 | 256.7 | 88.15 | 30.02 |

EXAMPLE 4

In accordance with the method in Example 1, a CVP-added mucosal vaccine having an AD vehicle amount of 0.3 μg and an HA antigenic protein amount of 0.03 μg was prepared. The mixing ratio of the HA antigenic protein, the AD vehicle and CVP was identical to that in Example 1 (i.e., containing the AD vehicle in an amount 10 times the antigenic protein amount and CVP at a final concentration of 0.5%).

EXPERIMENT 4

Each CVP-added mucosal vaccine of Example 1 (AD vehicle: 2.0 μg, HA antigenic protein amount: 0.2 μg) and Example 4 (AD vehicle: 0.3 μg, HA antigenic protein amount: 0.03 μg) was administered to mice (10 animals in each group) similarly to Experiment 1, which was then infected at day 14 after the second booster vaccination (immunization 3 times in total) with 50 PFU and 800 PFU of an influenza virus (A/PR8(N1H1)/μL).

Figure 4:
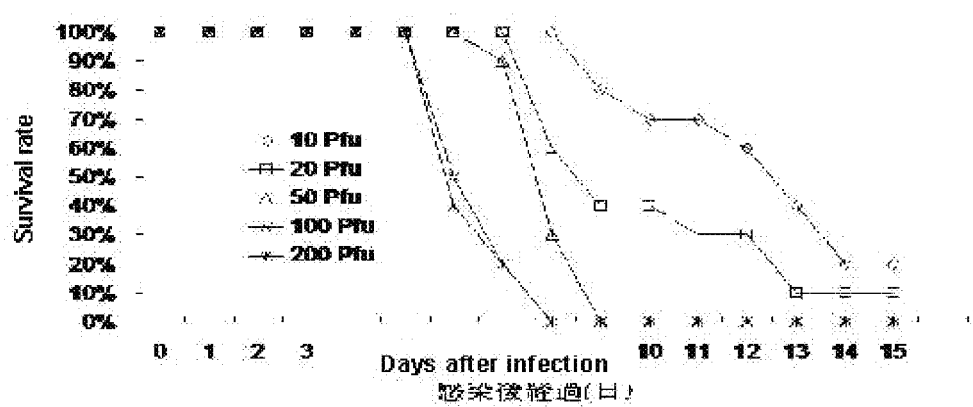
FIG. 4 The results of Experiment 4, which indicate the relationship between the PFU amount of the infected influenza virus and the survival rate.

As shown in FIG. 4, the infecting viral amount capable of obtaining a 50% lethal dose (LD50) was PFU<5, and in the absence of the vaccine treatment all mice died within 9 days at 50 PFU and 8 days at 100 PFU or more after the infection.

Figure 5:
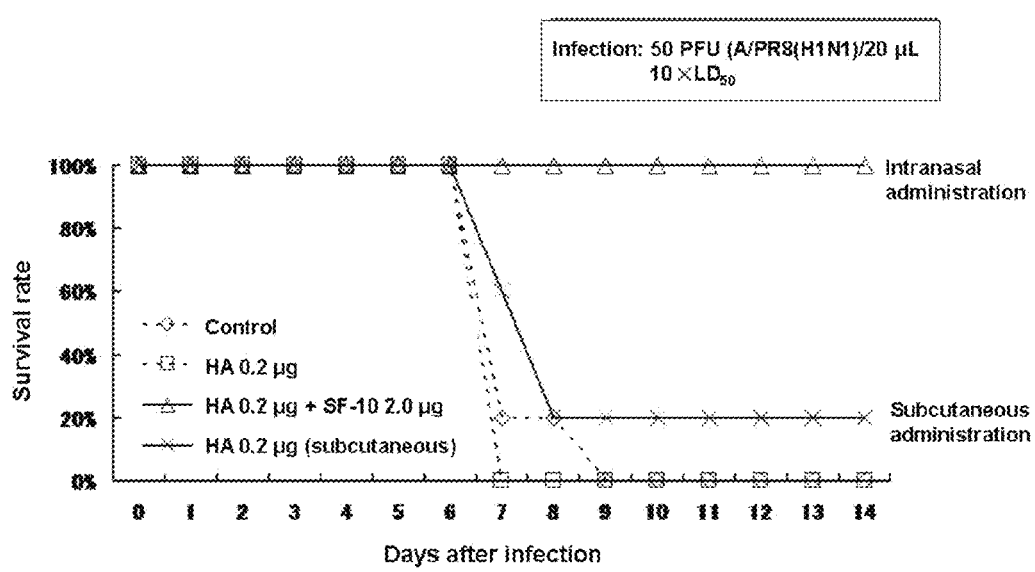
FIG. 5 The results of Experiment 4, which are the changes in the % survival when the mice (10 mice per group) were immunized intranasally with either of the vaccines of Example 1, Example 5, Comparative Example 5 or Comparative Example 6, and then infected with 50 PFU of the influenza virus.
Figure 6:
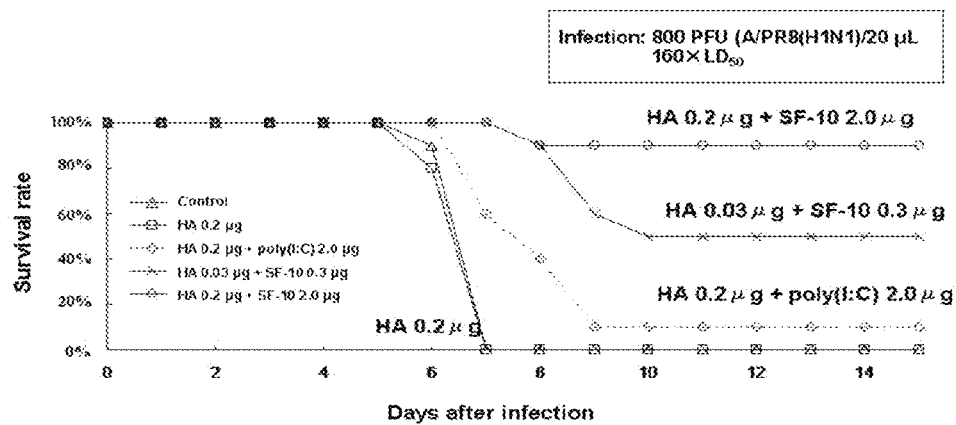
FIG. 6 The results of Experiment 4, which are the changes in the % survival when the mice (10 mice per group) immunized intranasally with either of the vaccine of Example 1, Example 5, Comparative Example 5 or Comparative Example 6, and then infected with 800 PFU of the influenza virus.

The effect of the vaccination on the survival rate was shown in FIG. 5 and FIG. 6. In both of the control (physiological saline) and Comparative Example 6 (HA antigenic protein only), all animals died within 7 to 9 days after viral infection with 50 PFU and 7 days after viral infection with 800 PFU. In Comparative Example 5 (HA+poly (I:C)), 9 out of 10 animals died within 9 days after the viral infection with 800 PFU.

On the other hand, the mice treated with the CVP-added mucosal vaccines of Example 1 and Example 4 all survived for 15 days after viral infection with 50 PFU. The viral infection with 800 PFU killed 1 out of 10 animals treated with the vaccine of Example 1 (after 8 days or later) and 5 out of 10 animals treated with the vaccine of Example 4 (after 10 days or later).

Based on these results, the CVP-added mucosal vaccine of the invention was confirmed to have an excellent infection preventing effect.

EXAMPLE 5

[Manufacturing Process B Involving No Ultrasonic Treatment]

A freeze dried AD vehicle powder was dissolved in a pure water and added to the HA antigenic protein fluid similar to that in Example 1, and then this mixture solution was combined with an equal quantity of a 1.0% CVP dissolved in a pure water to prepare a suspension. This suspension was warmed, without ultrasonic treatment, at 42° C. for 10 minutes using a water bath, and at the times of 3 and 7 minutes during the warming treatment the solution was stirred using a mixer for 10 seconds to achieve uniformity. After the warming treatment, the suspension was frozen overnight at −30° C. to −75° C., and lyophilized to make a dried powder. The freeze dried powder was stored at −30° C. Just before use, the freeze dried powder was suspended in physiological saline to obtain a CVP-added mucosal vaccine. The vaccine solution was adjusted so that 4 μl in total to be administered to the both nasal cavities of a mouse with 2 μl being given to each nostril a solution containing CVP at 0.5%, 0.2 μg of the HA antigenic protein and 2.0 μg of the AD vehicle phospholipid. Hereinafter this CVP-added mucosal vaccine is designated as HA+SF-10-B.

EXAMPLE 6

[Manufacturing Process C Involving No Ultrasonic Treatment]

A freeze dried AD vehicle powder dissolved in a pure water was admixed with the HA antigenic protein fluid similar to that in Example 1. This suspension was warmed at 42° C. for 10 minutes using a water bath, and at the times of 3 and 7 minutes during the warming treatment the solution was stirred using a mixer for 10 seconds to achieve uniformity. After the warming treatment, the suspension was frozen overnight at −30° C. to −75° C., and lyophilized to make a dried powder. The freeze dried powder was stored at −30° C. Just before use, the freeze dried powder was stirred gently with a 0.5% CVP solution previously dissolved in physiological saline while avoiding any foaming to obtain a CVP-added mucosal vaccine. Four μl in total to be administered to the both nasal cavities of a mouse with 2 μl being given to each nostril a solution containing 0.2 μg of the HA antigenic protein and 2.0 μg of the AD vehicle phospholipid. Hereinafter this CVP-added mucosal vaccine is designated as HA+SF-10-C.

EXPERIMENT 5

Each CVP-added mucosal vaccine of Example 1 (hereinafter designated as "HA+SF-10-A"), Example 5 (HA+SF-10-B), and Example 6 (HA+SF-10-C) was inoculated to mice (10 animals in each group) similarly to Experiment 1 (three times at intervals of 2 weeks), and the anti-influenza IgA and IgG antibodies were measured similarly to Experiment 1.

The results are shown in Table 4. Example 6 (HA+SF-10-C) exhibited an antibody inducing effect about 2 to 4 times for the IgA level and about 2 times for the IgG level, when compared with Example 1 (HA+SF-10-A) and Example 5 (HA+SF-10-B). Thus, the method of Example 6 (Manufacturing Process C) was assumed to result in its excellent antibody inducing effect because no ultrasonic treatment step is involved and the CVP solution is added in the final step.

TABLE 4

Comparison of antibody inducing effects by difference in vaccine manufacturing process Anti-influenza A/New Caledonia antibody titre (μg/mL)

|  | Physiological saline | HA | HA-SF-10 (Step A) | HA-SF-10 (Step B) | HA-SF-10 (Step C) |
|---|---|---|---|---|---|
| Nasal IgA | 0.01 ± 0.01 | 0.28 ± 0.12 | 4.98 ± 0.73* | 10.65 ± 2.52* | 24.06 ± 2.24* |
| Serum IgG | 0.06 ± 0.04 | 5.64 ± 0.48 | 624.10 ± 59.01* | 586.27 ± 52.3* | 1264.48 ± 143.55* |

EXPERIMENT 6

Figure 7:
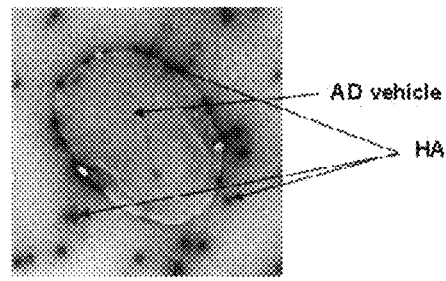
FIG. 7 Transmission electron microscope images, the results of Experiment 6. (A) The mucosal vaccine of Comparative Example 1, (B) CVP-added mucosal vaccine of Example 1 and the partially magnified image thereof (right figure).
Figure 7:
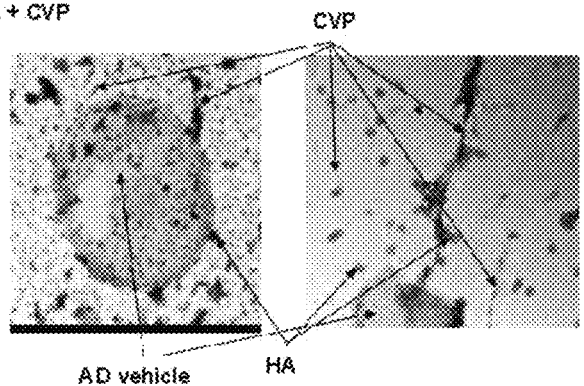

The form of each component in the CVP-added mucosal vaccines of the invention (HA antigenic protein, AD vehicle and CVP) was analyzed by a transmission electron microscope. As shown in FIG. 7, CVP played a role in a substantial increase in the binding between the antigen and the AD vehicle.

CVP has been employed as a thickening agent (Patent Documents 5 and 6) which is one of thickening polymers for improving the residence of an active ingredient in the nasal cavity in the same manner as hydroxypropyl cellulose (Patent Document 4), sodium alginate (Patent Document 7) and other excipients. However, as shown by the results of Experiment 6, CVP in the present invention was revealed, in a combination with the AD vehicle, to enhance the binding between the antigen and the AD vehicle, and to increase the amount of the antigen to be incorporated into the antigen presenting cells, thus enhancing the AD vehicle effect.

EXPERIMENT 7

SF-10 (AD vehicle+CVP) (20 μg) of Example 1 and the HA antigenic protein (2 μg) of Example 1 which was labeled with a fluorescent dye ATTO 488 were mixed and then added to the mouse bone marrow-derived dendritic cells ($2\times10^5$ cells), and after 1 hour incubation the fluorescence intensity of the dendritic cell labeled with the fluorescent dye-labeled HA antigenic protein was measured by a flow cytometry. Also the poly (I:C) (10 μg) of Comparative Example 5 and the fluorescent-labeled HA antigenic protein (2 μg) were mixed and the fluorescence intensity of the dendritic cells was measured similarly. The fluorescence exhibited by the dendritic cells reflects the binding and incorporation of the fluorescent dye-labeled HA antigenic protein to the cells.

Figure 8:
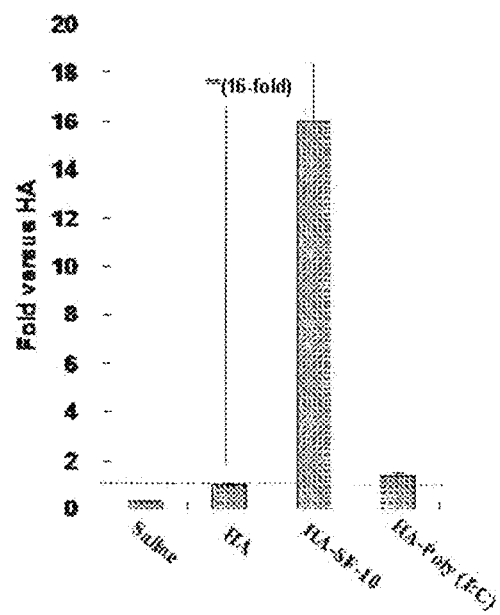
FIG. 8 The results of the flow cytometry in Experiment 7, which show the amount of the fluorescence-labeled antigen detected in dendritic cells. Providing that the fluorescence levels detected in the dendritic cells treated only with the HA antigen is 1, by how many folds of increase in the amount of the fluorescence were promoted under the each measurement condition is indicated on the ordinate with "Fold versus HA"=[MFI at each sample measurement]/[MFI in dendritic cell treated only with HA]. MFI: Mean Fluorescence Intensity **: $p<0.01$ vs. HA (n=3).

The results are shown in FIG. 8. While poly(I:C) did not promote the binding and the incorporation of the fluorescent dye-labeled HA antigenic protein to the dendritic cells, SF-10 exhibited a significant promoting effect.

Based on these results, the SF-10 mucosal vaccine of the invention was confirmed to promote the binding and the incorporation of the antigenic protein to the antigen presenting cells thereby increasing the antibody production and exerting an excellent infection preventing ability.

EXPERIMENT 8

The followings were added to the cultured mouse bone marrow-derived dendritic cells ($2 \times 10^5$ cells) in 1 mL of cRPMI medium, and the activation of the dendritic cells after 1 hour was measured by a flow cytometry employing as an index of the increase in the expression of CD86 which is one of the dendritic cell activation markers. FACSCalibur cytometer (BD Biosciences, Massachusetts, United States) was used for measurement and CellQuest software (BD Biosciences, Massachusetts, United States) was used for data processing to determine the CD86 expression.
  Physiological saline
  Physiological saline+HA antigenic protein
  SF-10
  SF-10+HA antigenic protein
  Poly (I:C)
  Poly (I:C)+HA antigenic protein The HA antigenic protein (2 μg) and SF-10 (20 μg) were those described in Example 1, while Poly (I:C) (10 μg) was identical to that in Comparative Example 5.

Figure 9:
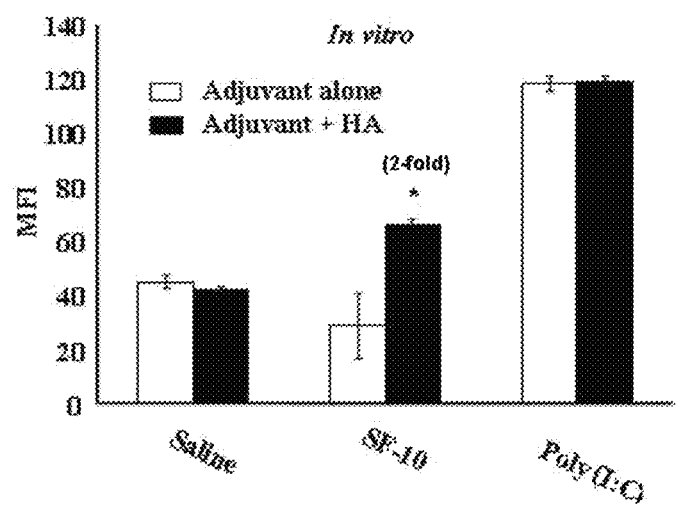
FIG. 9 The result of Experiment 8, in which the expression levels of activation marker molecule (CD86) on the cell membrane were measured when antigen presenting dendritic cells were stimulated with poly(I:C) and SF-10 (CVP+ AD vehicle), respectively. The □ indicates the absence of HA antigenic protein, while the ■ indicates the presence of HA antigenic protein. MFI: Mean Fluorescence Intensity, *: $p<0.05$ vs.Adjuvant alone (n=3).

The results are shown in FIG. 9. While Poly (I:C) by itself increased the expression of CD86 (activation marker of the dendritic cells) similarly to Experiment 2, the expression of CD86 was not further increased even when adding the antigen. On the contrary, SF-10 did not activate the dendritic cells per se, but the CD86 expression in the presence of the antigen was enhanced by about 2 times.

Based on these results, the CVP-added mucosal adjuvant of the invention, i.e., SF-10, was assumed to deliver the antigen effectively to the antigen presenting dendritic cells to activate them thereby inducing the antibody production.

The similar results were obtained when using CD40 which is also one of the dendritic cell activation markers.

EXPERIMENT 9

In order to examine the dendritic cell-activation due to an increased antigen delivery by SF-10 which was confirmed in vitro in Experiment 8, in an individual mouse (in vivo), the followings identical to those in Experiment 8 were administered into the nasal cavities of the mouse.
  Physiological saline
  Physiological saline+HA antigenic protein
  SF-10
  SF-10+HA antigenic protein The animal experiment was along the line with Experiment 1. The HA antigenic protein (0.2 μg) and SF-10 (2 μg) were those of Example 1, while Poly (I:C) (2 μg) was identical to that in Comparative Example 5.

The mouse was decapitated 48 hours after the nasal inoculation and the tissues in the nasal cavities were collected and treated with a collagenase (1 mg/mL, shaking at 37° C. for 30 minutes). After filtration through a mesh followed by centrifugation (4° C., 10 min, 200×g), dendritic cells were prepared from the recovered cells by VarioMACS (Miltenyl Biotech, Bergisch Gladbach, Germany) using Anti-CD11c (N-418)-conjugated magnetic beads (Miltenyl Biotech, Bergisch Gladbach, Germany) and LS column, in accordance with the manufacture's instruction. Then, the expression enhancement of CD86 was measured by the method similar to that in Experiment 8.

Figure 10:
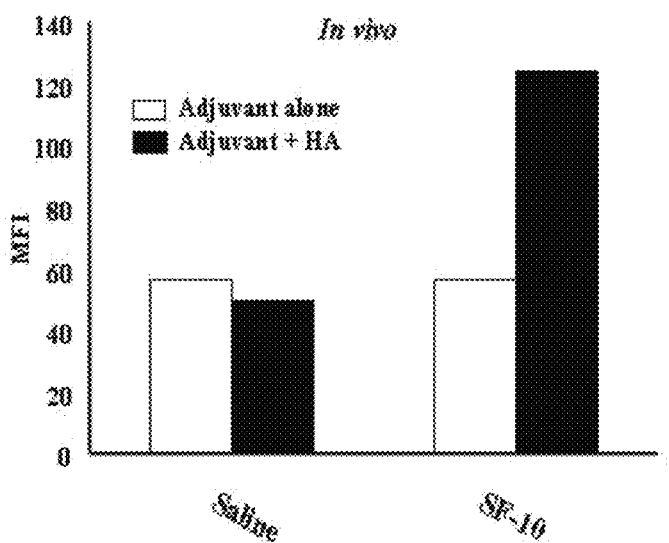
FIG. 10 The results of Experiment 9, in which CD86 expression levels on the membrane of dendritic cells prepared from a nasal cavity tissue of mice was measured. Mice were immunized intranasally with the SF-10 (CVP+AD vehicle) adjuvant in the presence or absence of the antigen. MFI: Mean Fluorescence Intensity.

The results are shown in FIG. 10. The dendritic cell-activation due to an increased antigen delivery by SF-10 was confirmed also in the nasal cavities of the mouse.

EXPERIMENT 10

CVP was investigated for its preferable concentration. Except for employing pAA130 manufactured by Sigma Corporation as CVP at concentrations of 0.1%, 0.25%, 0.5%, 0.75% or 1.0%, a CVP-added mucosal vaccine was prepared by the method of Example 6, and the amounts of mouse nasal wash antigen-specific IgA and serum IgG were measured by the method of Experiment 1.

The results are shown in Table 5, which indicates that both of IgA and IgG were enhanced in response to the increase in the CVP amount up to a CVP pAA130 concentration of 0.5%. After reaching the peak at 0.5% CVP, a higher concentration of CVP tended to rather reduce the antibody inducing effect.

TABLE 5

Effect of CVP concentration in HA-SF-10 mucosal vaccine

| | Anti-A/NewCaledonia antibody titer | |
|---|---|---|
| | Nasal wash IgA (μg/mL) | Serum IgG (μg/mL) |
| Physiological saline | 0.01 ± 0.01 | 0.06 ± 0.04 |
| HA | 0.28 ± 0.12 | 5.64 ± 0.48 |
| HA-SF-10 | | |
| CVP 0.1% | 9.52 ± 1.41 | 624.17 ± 59.53 |
| CVP 0.25% | 14.03 ± 1.31 | 488.16 ± 152.70 |
| CVP 0.5% | 24.06 ± 2.24 | 1264.48 ± 143.55 |
| CVP 0.75% | 14.18 ± 1.33 | 875.62 ± 82.90 |
| CVP 1.0% | 10.85 ± 1.42 | 875.60 ± 64.52 |

The invention claimed is:

1. A mucosal vaccine producing an antigen-specific mucosal IgA and blood IgG in the levels capable of exerting an effective immune induction and an infection-preventing effect, which comprises:
   (a) an AD vehicle consisting of a synthetic peptide and a lipid(s), wherein the synthetic peptide consisting of the amino acid sequence KnLm (wherein n is 4 to 8 and m is 11 to 20);
   (b) a carboxyvinyl polymer; and,
   (c) an antigenic protein in an amount of $\frac{1}{5}$ or less of the amount required for producing a sufficient mucosal IgA and blood IgG in a mucosal vaccine consisting of said AD vehicle and the antigenic protein.

2. The mucosal vaccine of claim 1, wherein the antigen protein (c) is in an amount, even in combination with the AD vehicle (a) or in combination with the carboxyvinyl polymer (b), incapable of producing an antigen-specific mucosal IgA and a blood IgG in amounts capable of exerting an effective immune induction and an infection-preventing effect.

3. The mucosal vaccine of claim 1, wherein the synthetic peptide consists of the amino acid sequence of SEQ ID NO: 1 or 2.

4. The mucosal vaccine of claim 1, wherein the lipid is at least one of phosphatidyl choline, dipalmitoylphosphatidyl choline, phosphatidyl serine, phosphatidyl glycerol, phosphatidyl inositol, phosphatidyl ethanolamine, phosphatidic acid, lauric acid, myristic acid, palmitic acid, stearic acid and oleic acid.

5. The mucosal vaccine of claim 3, wherein the lipids are a mixture of dipalmitoylphosphatidyl choline, phosphatidyl glycerol and palmitic acid.

6. The mucosal vaccine of claim 1, wherein the antigenic protein is a pathogen-derived inactivated antigen, a purified antigen, a partially purified antigen, a recombinant antigen, a detoxicated toxin or an allergen causative of an allergy.

7. A method for producing a mucosal vaccine producing an antigen-specific mucosal IgA and a blood IgG in the levels capable of exerting an effective immune induction and an infection-preventing effect, which comprises:
   (a) an AD vehicle consisting of a synthetic peptide and a lipid(s), wherein the synthetic peptide consisting of the amino acid sequence KnLm (wherein n is 4 to 8 and m is 11 to 20);
   (b) a carboxyvinyl polymer; and,
   (c) an antigenic protein in an amount of $\frac{1}{5}$ or less of the amount required for producing a sufficient mucosal IgA and blood IgG in a mucosal vaccine consisting of said AD vehicle and the antigenic protein,
   which method comprises:
   (1) suspending said (a) and (c) in water;
   (2) repeating warming and stirring once or more;
   (3) freezing and lyophilizing,
   (4) suspending the lyophilized form in physiological saline to adjust to a predetermined concentration; and,
   (5) adding a solution of said (b).

\* \* \* \* \*

SEQUENCE LISTING

<160> NUMBER OF SEQ ID NOS: 2

<210> SEQ ID NO 1
<211> LENGTH: 22
<212> TYPE: PRT
<213> ORGANISM: artificial

```
<220> FEATURE:
<223> OTHER INFORMATION: Description of artificial sequence: synthetic
      peptide

<400> SEQUENCE: 1

Lys Lys Lys Lys Lys Lys Leu Leu Leu Leu Leu Leu Leu Leu Leu Leu
1               5                   10                  15

Leu Leu Leu Leu Leu Leu
            20

<210> SEQ ID NO 2
<211> LENGTH: 17
<212> TYPE: PRT
<213> ORGANISM: artificial
<220> FEATURE:
<223> OTHER INFORMATION: Description of artificial sequence: synthetic
      peptide

<400> SEQUENCE: 2

Lys Lys Lys Lys Lys Lys Leu Leu Leu Leu Leu Leu Leu Leu Leu Leu
1               5                   10                  15

Leu
```